US007611614B2

(12) United States Patent
Reel et al.

(10) Patent No.: US 7,611,614 B2
(45) Date of Patent: Nov. 3, 2009

(54) METHOD OF CELL CAPTURE

(75) Inventors: Richard T. Reel, Hayward, CA (US);
Eric S. Nordman, Palo Alto, CA (US);
Zbigniew T. Bryning, Campbell, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 824 days.

(21) Appl. No.: 11/338,255

(22) Filed: Jan. 24, 2006

(65) Prior Publication Data
US 2006/0124463 A1 Jun. 15, 2006

Related U.S. Application Data

(63) Continuation of application No. 09/938,894, filed on Aug. 24, 2001, now Pat. No. 7,014,744.

(51) Int. Cl.
*B03C 5/00* (2006.01)
*B01D 57/02* (2006.01)

(52) U.S. Cl. .............. 204/450; 204/547; 204/643; 435/173.9

(58) Field of Classification Search ........... 204/450, 204/547, 600, 643; 435/173.9
See application file for complete search history.

(56) References Cited

U.S. PATENT DOCUMENTS

| 4,124,470 A | 11/1978 | Dahms |
| 4,326,934 A | 4/1982 | Pohl |
| 4,643,814 A | 2/1987 | Goldstein |
| 4,699,881 A | 10/1987 | Matschke |
| 4,767,514 A * | 8/1988 | Candor ...................... 204/547 |
| 4,911,806 A | 3/1990 | Hofmann |
| 5,164,055 A | 11/1992 | Dubrow |
| 5,304,486 A | 4/1994 | Chang |
| 5,422,272 A | 6/1995 | Papp et al. |
| RE35,102 E | 11/1995 | Zare et al. |
| 5,593,559 A | 1/1997 | Wiktorowicz |
| 5,985,119 A | 11/1999 | Zanzucchi et al. |
| 5,989,402 A | 11/1999 | Chow et al. |
| 6,203,683 B1 | 3/2001 | Austin et al. |
| 6,277,257 B1 | 8/2001 | Paul et al. |
| 6,306,590 B1 | 10/2001 | Mehta et al. |
| 6,375,817 B1 | 4/2002 | Taylor et al. |
| 6,413,401 B1 | 7/2002 | Chow et al. |
| 2001/0052460 A1 | 12/2001 | Chien et al. |

FOREIGN PATENT DOCUMENTS

| WO | WO 92/08517 A1 | 5/1992 |
| WO | WO 97/08293 A1 | 3/1997 |
| WO | WO 97/41219 A1 | 11/1997 |
| WO | WO 00/49173 A2 | 8/2000 |
| WO | WO 01/07452 A1 | 2/2001 |

OTHER PUBLICATIONS

Supplementary European Search Report, completion date Jan. 18, 2005, for European Application No. EP 02 76 6066 (2 pages).
Search Report from PCT/US02/26827 Mailed Jun. 12, 2002.

* cited by examiner

*Primary Examiner*—Kaj K Olsen
(74) *Attorney, Agent, or Firm*—Andrew K. Finn; Life Technologies Corp.

(57) ABSTRACT

Embodiments of methods and devices are disclosed for the manipulation (e.g., concentration, purification, capture, trapping, location, transfer) of analytes, e.g., biomolecules, with respect to analyte-containing solutions, using one or more electric fields.

16 Claims, 4 Drawing Sheets

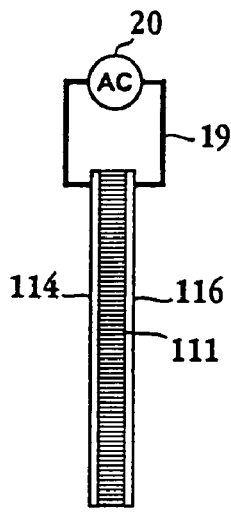 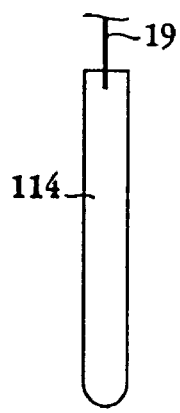 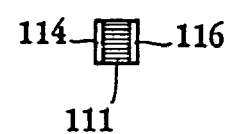 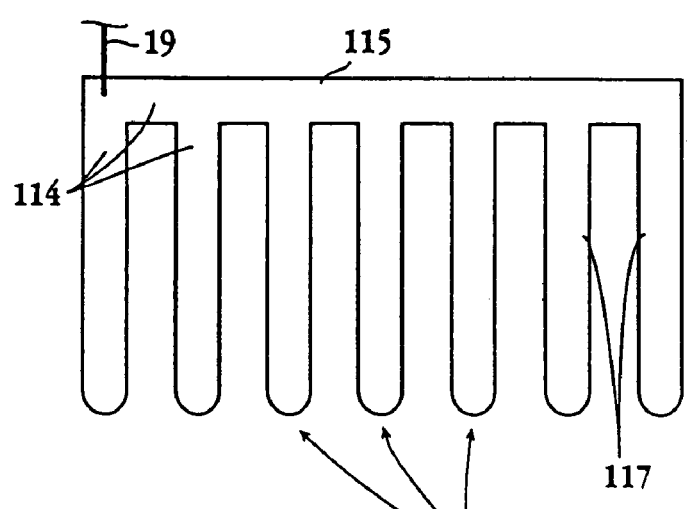 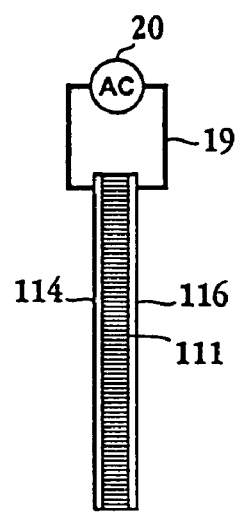
Fig. 5A      Fig. 5B      Fig. 5C
Fig. 5D      Fig. 5E

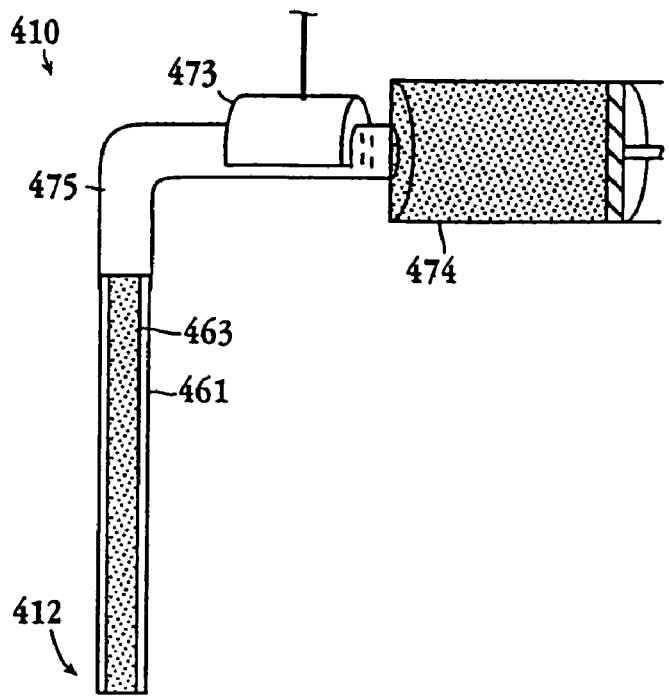
Fig. 9A
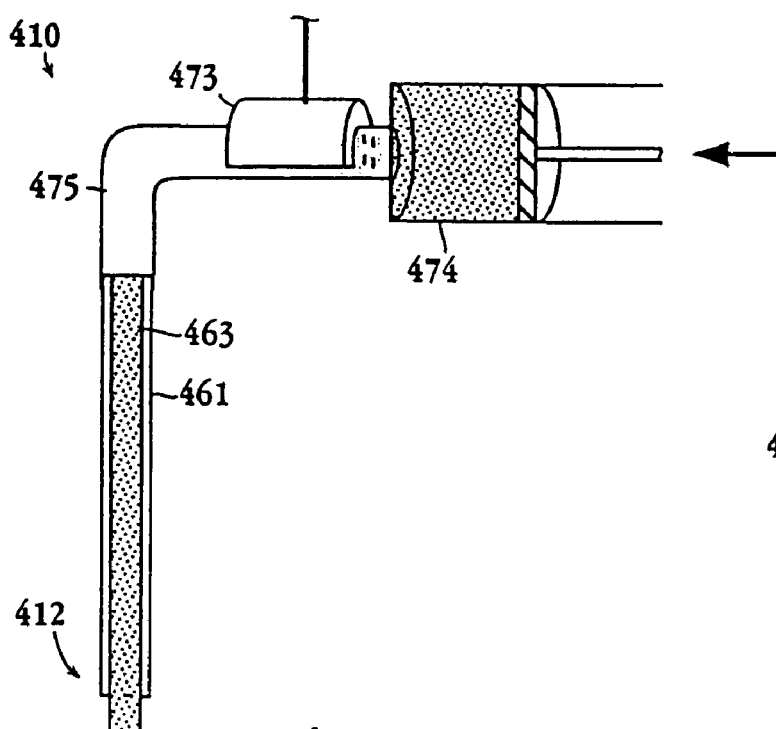 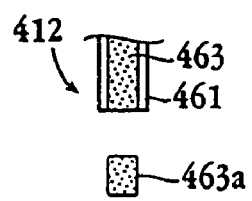
Fig. 9B       Fig. 9C

METHOD OF CELL CAPTURE

CROSS-REFERENCE TO RELATED APPLICATIONS

This application is a continuation of U.S. patent application Ser. No. 09/938,894 filed on Aug. 24, 2001, now U.S. Pat. No. 7,014,744, which is incorporated herein by reference in its entirety.

FIELD OF THE INVENTION

This invention relates to methods and apparatus for the manipulation of analytes using electric fields.

BACKGROUND

In many chemical and biochemical methods and/or applications, it is often desirable to at least partially concentrate or purify a sample or analyte. For example, increased analyte concentration can enhance chemical reaction rates, rates of mass transfer, and/or detectability, etc. In addition, methods for controlling the location of at least a portion of a sample or analyte can be important in many chemical and biochemical methods and/or applications.

SUMMARY

An aspect of the present invention is directed towards methods and devices for the manipulation (e.g., concentration, purification, capture, trapping, location, transfer, and the like) of polarizable analytes, such as polynucleotides, using one or more electric fields.

An embodiment of the present invention relates, in part, to a device and method for purification/concentration of an analyte away from a processor and/or analyzer (e.g., a capillary electrophoresis device, an optical reader, a mass spectrometer, a chromatographic column, a PCR device, etc.). In an embodiment, a device and method of the present invention are useful in transferring a purified/concentrated sample to a desired location, such as to a sample-receiving region of such a processor and/or analyzer, and/or to a vessel such as a tube or a well of a multi-well plate.

An embodiment of the invention makes use of the phenomenon that if a molecule or particle can be polarized, then it can be attracted or repelled from a field gradient. Certain embodiments of the invention are based in part on the discovery that when a polarizable analyte is attracted to a region having an alternating current electrical field gradient, the analyte can become trapped in a concentration zone formed by the alternating electric field. Various embodiments of the present invention, for example, contemplate polynucleotides, e.g., DNA or RNA, as polarizable molecules of interest, and utilize increasing field gradients to attract such molecules. One of the many applications of the present invention is to partition, at least in part, DNA from salts or free dyes.

An aspect of the present invention provides an analyte-manipulation device for moving a polarizable analyte of interest, such as DNA or RNA, with respect to a sample holder (e.g., vial, tube, well, container, etc.) configured to hold such analyte. In an embodiment, the device includes: at least two coextensive, elongated, electrically-conductive members disposed in spaced apart relation with respect to one another; with the members and the holder being adapted for relative movement between a first position wherein at least a portion of the members (e.g., lower end regions) is disposed within the holder and a second position wherein the members are disposed outside (e.g., spaced apart or away from) of the holder; an AC power source adapted for electrical communication with the electrically-conductive members; wherein, with the members and holder disposed at the first position, the AC power source is operable in combination with the electrically-conductive members to establish an electrical field gradient within the holder, between the end regions.

Another aspect of the present invention provides an analyte-manipulation device for moving a charged analyte (e.g., biomolecule) of interest with respect to a sample holder (e.g., vial, tube, well, container, etc.) configured to hold such analyte. In an embodiment, the device includes: at least two coextensive, elongated, electrically-conductive members disposed in spaced apart relation; with the members and the holder being adapted for relative movement between a first position wherein at least a portion of the members (e.g., lower end regions) is disposed within the holder and a second position wherein the members are disposed outside of (e.g., spaced apart or away from) the holder; wherein at least one of the members is a bubble-free electrode; a DC power source adapted for electrical communication with the electrically-conductive members; wherein, with the members and holder disposed at the first position, the DC power source is operable in combination with the electrically-conductive members to establish an electrical potential within the holder, between the members.

Numerous other advantages and features of the present invention will become apparent from the following detailed description of the invention and the embodiments thereof, from the claims and from the accompanying drawings.

BRIEF DESCRIPTION OF THE DRAWINGS

FIG. 5A is a partially schematic view from one side of a device for manipulating analytes, according to an embodiment of the present invention;

FIG. 5B is a partial view from another side of the device of FIG. 5A;

FIG. 5C is a view from beneath the device of FIG. 5A;

FIGS. 5D and 5E are partially schematic views from a side and from one end, respectively, of a device for manipulating analytes, according to an embodiment of the present invention;

FIGS. 9A and 9B are partially schematic side views of an embodiment of a device for manipulating analytes, according to the present invention; and FIG. 9C is a view of an end region of the device of FIGS. 9A and 9B, showing a gel-like electrolyte (slug) discharged therefrom.

Structural elements having similar or identical functions may have like reference numerals associated therewith. The appended drawings illustrate only typical embodiments of this invention and are not limiting of its scope, for the invention may admit to other equally effective embodiments.

DETAILED DESCRIPTION OF THE PREFERRED EMBODIMENTS

Figure 1A:
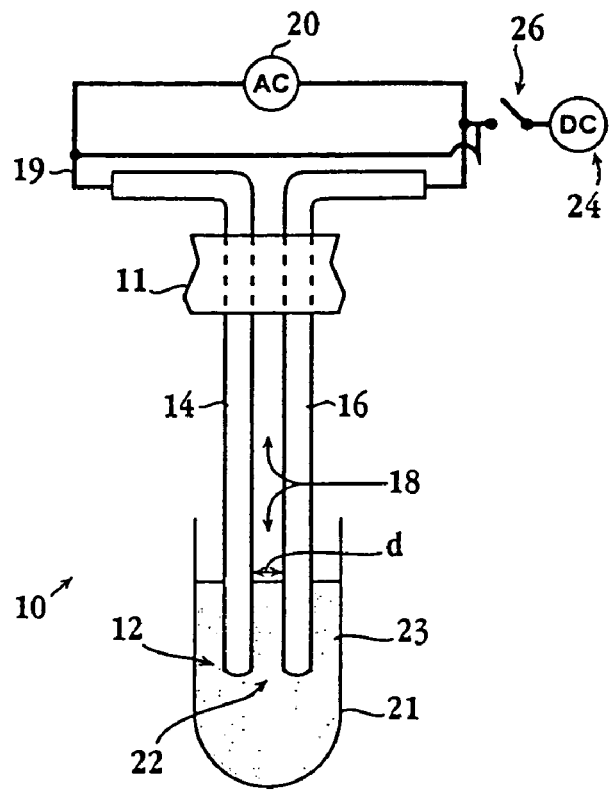
FIGS. 1A and 1B are partially schematic, side and bottom views, respectively, of a device for manipulating analytes, according to the teachings of the present invention.

Reference will now be made in detail to certain preferred embodiments of the present invention, examples of which are illustrated in the accompanying drawings. While the invention will be described in conjunction with selected preferred embodiments, it will be understood that these embodiments are not intended to in any way limit the scope of the invention. On the contrary, the invention is intended to cover alternatives, modifications, and equivalents, which may be included within the scope of the invention as determined by the appended claims.

As used herein, the term "purified" means that a material is removed from an original or starting state or environment. For example, a material is said to be "purified" when it is present in a particular composition in a higher concentration than exists as it is found in a starting sample. For example, where a starting sample comprises a polynucleoticle in a crude cell lysate, the polynucleotide can be said not to be purified, but the same polynucleoticle separated from some or all of the coexisting materials in the cell lysate is purified.

Generally, the present invention relates to methods and apparatus for the manipulation (e.g., purification, concentration, capture, trapping, location, transfer, and the like) of analytes (e.g., bio-molecules) using one or more electric fields.

An aspect of the present invention makes use of field gradients to concentrate and purify analytes in samples, including gradients formed by application of an AC field. Essentially any analyte that can be polarized in an electric field, e.g., molecules or suspended particles, can be manipulated using generated field gradients. The inventors hereof have found that polarizable analytes can be attracted to regions of high field gradients, such as those generated near electrode edges or points. Further, in some cases, polarizable analytes can be repelled from regions of high field gradient. Attraction to and/or repulsion from regions of high field gradients are exploited herein as a means of concentrating polarizable particles, e.g., from a bulk solution.

In various embodiments, applied fields useful to attract or repulse a polarizable analyte are generated by way of an alternating current, or AC, power source. Preferably, the field is divergent at one or more points or regions in order to form field gradients to attract or repulse the analytes.

Using attractive and/or repulsive concentration, a polarizable analyte can be located and concentrated relative to a bulk solution. Additionally, by selecting appropriate electric field parameters, a polarizable analyte can be purified relative to other species in a bulk solution that are less polarizable under the applied electric field. These less-polarizable analytes will feel a relatively smaller attraction or repulsion due to the applied field and will not be as readily concentrated as will the more polarizable analyte. This difference in selectivity for species based on attraction or repulsion to high field gradients can form the basis for concentration and purification of one or more species from a complex mixture.

Aspects of the present invention are particularly useful in connection with analytes that have a dipole moment. The analyte may be charged or uncharged; it may have an overall net charge or be neutral. According to various embodiments, the analyte is present in a buffered electrolyte solution, e.g., an electrolyte solution having a low ionic strength. Exemplary analytes include nucleic acids, both single and double stranded, proteins, carbohydrates, viruses, cells, organelles, organic polymers, particles, and the like. In certain embodiments, a preferred analyte for use with the present invention is single or double stranded nucleic acid contained in an electrolyte solution.

Figure 1B:
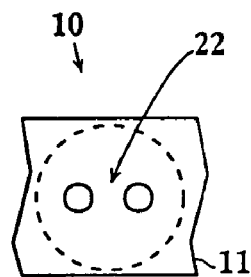

In an embodiment of the invention, and with reference to FIG. 1, an analyte-manipulation device, denoted generally as 10, is configured to create a field gradient; e.g., at a tip region, such as is shown at 12. The device 10 comprises a support 11 holding spaced-apart, co-extensive, elongate, electrically-conductive members, such as electrodes or wires 14, 16. Members 14, 16 can be held in any suitable fashion. In certain preferred embodiments, members 14, 16 are held in a fashion permitting the members to move as a unit with support 11. For example, members 14, 16 can be fixedly attached to support 11. In one embodiment, members 14, 16 are firmly, yet removably, received within respective mounting holes formed through the support.

An elongate narrow gap region 18 is defined between confronting side regions of members 14, 16. In an embodiment, with continued reference to FIG. 1, the dimension d of gap region 18 is within a range of from 20 µm and 1.50 mm. In a particular embodiment, the dimension d is between about 100 µm and 0.75 mm. Members 14, 16 are disposed for electrical communication, via circuitry 19, with an alternating current (AC) power supply 20 for providing a time-variant voltage difference therebetween. A concentration zone, indicated generally in the area denoted at 22, is located along a submerged portion of the gap region 18, between members 14, 16; and particularly near the tip region 12.

In use, the tip region 12 of the device 10 can be dipped into a sample containing one or more analytes of interest, such as the DNA-containing sample 23 held in tube or well 21 shown in FIG. 1A. For example, where the analyte of interest is a polynucleotide such as DNA, the DNA will be preferentially attracted to an increasing field gradient established in the gap region 18 between members 14 and 16; and particularly along the concentration zone 22. In an embodiment, the gap region 18 is configured to hold a defined volume of liquid, e.g., in a fashion similar to that of a quill pen. The tip region 22 can then be moved to a receiving region (e.g., a clean, empty well of a microtitre plate) were the DNA can be deposited, e.g., upon discontinuing the AC field. The deposition of DNA into the receiving region can be expedited by applying a negative voltage to members 14, 16 to drive the DNA off the tip region (due to the repulsive effects of such negative voltage with respect to the negatively charged phosphate groups of the DNA). FIG. 1A illustrates a DC power source 24 electrically connectable to (and disconnectable from) members 14, 16 by way of a switch 26 for such purpose.

Under circumstances where the receiving region (e.g., a vessel, such as a tube or well), whereat the DNA is deposited, contains a smaller amount of liquid the than the starting volume from which the DNA was taken, the DNA will thereby be concentrated. In addition, where the DNA is taken from a sample containing salts, the presently described device and method can assist in desalting the sample, since the tip region will not preferentially attract salts (as salts are not readily polarized). Among the many advantages that can be realized by way of the present teachings, the combination of these two events (concentration and desalting) can result in an increase in the amount of analyte available for injection into a separation channel during a DNA analysis.

Optionally, the device 10 can further include a detector (not shown) positioned such that material located in the concentration zone 22 may be detected. In addition, the device 10 can further optionally include a computer (not shown) connected to one or both of power supplies 20, 24, and/or to the detector (not shown), for example, to control and monitor the operation of the device and to manage the acquisition, analysis, and presentation of data.

Figure 2:
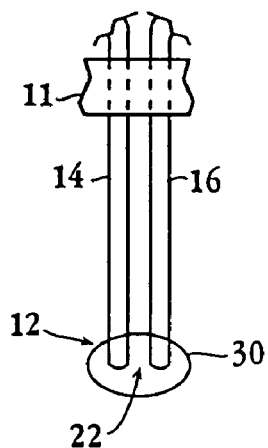
FIG. 2 is a side partial view of an embodiment of a device for manipulating analytes, according to the present invention.

In an embodiment of the present invention, and with reference now to FIG. 2, device 10 includes elongate members 14, 16 with tip regions (generally at 12) that are potted in a non-conductive material, such as a bead of resin 30, or other non-conducting material (e.g., an epoxy material, or the like). This can be useful, for example, to assist in maintaining a set (defined) spacing between the opposed tip regions.

Figure 3:
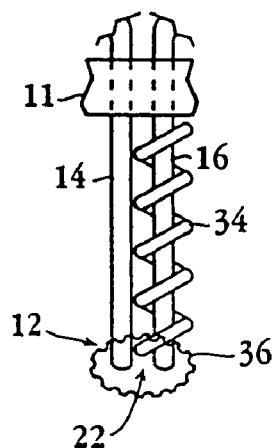
FIG. 3 is a side partial view of an embodiment of a device for manipulating analytes, according to the present invention.

In an embodiment of the invention, a nonconductive filament is wrapped around one or more of the elongate members of the device. For example, FIG. 3 illustrates a non-conductive filament 34 wrapped in a spiral or helical fashion around member 16. Suitable filament materials include nylon, Teflon, polyimide or other plastics, among others. The filament can be held in place against member 16, for example by tight wrapping and frictional forces and/or through the use of one or more adhesives and/or fastening devices. The arrangement of FIG. 3 can help to maintain a fixed spacing between members 14 and 16, as well as increase the amount of fluid the device will hold. In addition, or as an alternative, the tip regions of members 14, 16 can be encapsulated with a porous material (e.g., sponge-like), as at 36, to assist in holding fluid and keeping the members 14, 16 spaced apart.

Figure 4:
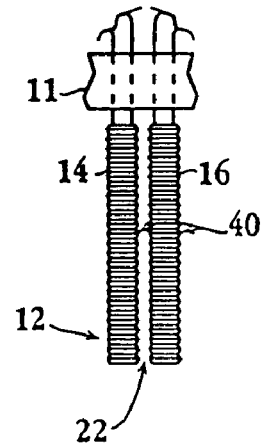
FIG. 4 is a side partial view of an embodiment of a device for manipulating analytes, according to the present invention.

It is noted that the wires need not be rod-like or cylindrical. A variety of geometries can be used to generate, tailor and even enhance (e.g., strengthen) the concentration of a field gradient. For example, surface features, such as points, sharp edges, corners, angles, bumps, protrusions, teeth, undulations, notches, indentations, waves, ripples, fins, or the like, can be provided along one or both of members 14, 16, e.g., in the vicinity of the tip regions. In one embodiment, one or both elongated members are configured much in the fashion of a self-tapping screw. Such features can be advantageous, for example, to form and/or enhance the field gradient. In an embodiment, illustrated in FIG. 4, sharp points or edges, indicated at 40, are formed along a majority of the length of each of members 14, 16 to each member's terminal end.

In an embodiment of the invention, an elongate non-conductive substrate is treated to provide conductive regions or paths therealong. For example, referring now to FIGS. 5A-5C, an elongate non-conductive substrate 111 bears separated coatings on opposite sides, as indicated at 114 and 116. In one embodiment, electrically conductive coatings are sprayed or deposited onto a suitable non-conductive substrate, such as a porous ceramic or polymeric substrate. Any suitable electrically conductive coating material can be used, e.g., metallic materials such as copper or aluminum, or electrically conductive resins or paints. In one embodiment a masking technique is employed to selectively deposit conductive materials.

The present invention further contemplates arrangements wherein a plurality of analyte-manipulation devices as described herein are held by a common support. FIGS. 5D-5E, for example, show a support 111 and a plurality of analyte-manipulation devices 110 depending therefrom. Each of devices 110 is substantially as described above with respect to FIGS. 5A-5C. As can be seen, for example, in FIG. 5D, this multiple-device arrangement can be configured substantially in the fashion of a comb having an upper elongate, substantially horizontally disposed body portion 115 and spaced apart elongate members 117, analogous to the teeth of a comb, depending therefrom. Body 115 and members 117 can be integrally formed, or formed separately and attached to another one another by any suitable means (e.g., an adhesive or riveting). In the depicted arrangement, body 115 and members 117 are comprised of a non-conductive material bearing coatings of conductive material on opposite major surfaces thereof to form electrical paths therealong. The conductive coatings are disposed for electrical communication, via appropriate circuitry 19, with an AC power source 20.

Figure 6:
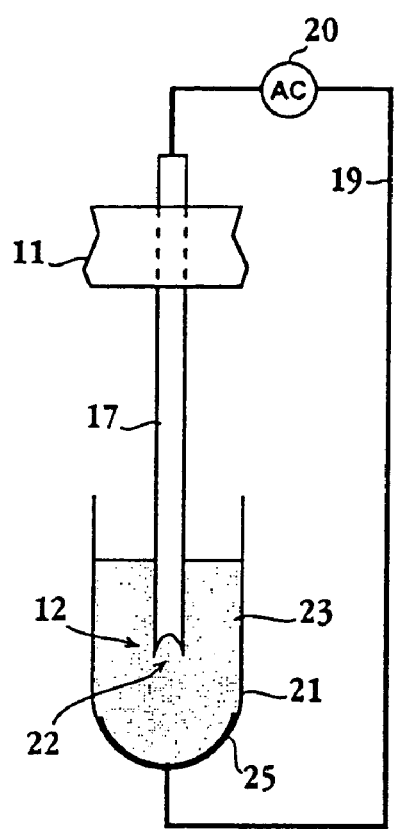
FIG. 6 is a partially schematic side view of a device for manipulating analytes, according to an embodiment of the present invention.

Another embodiment of the present invention includes a single elongate conductive member with a lower tip region and an AC power source. A receiving region in connection with which the device is used, such as well 21, can be electrically disposed (e.g., grounded) to provide a return path. As shown for example in FIG. 6, well 21 includes a conductive surface 25 lining an inner, lower region thereof, which is electrically coupled to AC power source 20. Surface 25 can be any substantially inert conductive material, such as a metallic layer. The DNA contained in a fluidic sample 23 held in well 21 will be preferentially attracted to the tip region 12 rather that the well 23 because the small surface will cause field gradients in the vicinity of the tip region 12. It should be appreciated that surface features (e.g., points, edges, etc.) or fluid capacity modifications, such as described above, can be employed in this embodiment.

According to an embodiment of the invention, an analyte-manipulation device of the present invention is configured for manual operation. For example, the support can be designed to be held in the hand of an operator, e.g., in a fashion similar to that of a manually-operable pipette, and readily moved from place to place (e.g., from a sample vessel to a receiving vessel).

In another embodiment of the invention, one or more analyte-manipulation devices, such as any of those described herein, are incorporated in an automated workstation, e.g., such as described in U.S. Pat. No. 6,132,582, entitled, "Sample handling system for a multi-channel capillary electrophoresis device" and/or in U.S. Pat. No. 6,159,368, entitled, "Multi-well Microfiltration Apparatus" (both of which are incorporated herein by reference). For example, the support can be adapted for automated positioning (e.g., x-y-z motion) permitting the device to address various regions or components of a workstation.

As previously indicated, the electrodes used to effect the alternating electric field can have a shape which serves to form an electric field that results in a defined concentration zone having desired dimensions. The spacing of the electrodes can be chosen so as to generate an electric field having sufficient strength to trap a polar analyte of interest, but not so high as to cause excessive bubble formation at the electrodes, e.g., see Washizu et al., *IEEE Transactions on Industry Applications*, 30 (4): 835-843 (1994). In an embodiment, the spacing (see dimension d, in FIG. 1) between the electrodes is between about 20 µm and 2 mm (e.g., about 0.75-1.0 mm).

The alternating electric field used to trap a polarizable analyte can be any alternating electric field effective to manipulate, e.g., capture and concentrate, such an analyte. Generally, the alternating electric field of the invention may be characterized by a time vs. field strength profile, a frequency, and a maximum field strength. The properties of the alternating electric field required to manipulate the analyte will depend on a number of readily accessible experimental parameters including, for example, the magnitude of the dipole moment of a polar analyte, the dielectric constant of the supporting medium, and, in the case of an analyte having an induced dipole moment, the polarizability of the polar analyte or surrounding counter-ion microenvironment.

The time vs. field strength profile of the alternating electric field may be sinusoidal, sawtooth, rectangular, superpositions of the foregoing, periodic or non-periodic, or any other profile capable of being generated using a suitable function generator, e.g., a Model 33120A 15 MHz Function/Arbitrary Waveform Generator from Agilent Technologies. In an embodiment of the invention, the time vs. field strength profile of the alternating electric field is rectangular. In one embodiment, the time vs. field strength profile of the alternating electric field is such that the time-averaged integrated field strength is zero where the average is taken over one complete cycle.

The frequency of the alternating electric field may be any frequency capable of manipulating a portion of a polarizable analyte. For many analytes of practical importance, for example, the frequency of the alternating electric field may be between about 10 Hz and 100 megahertz (MHz). In an embodiment of the invention, the frequency of the alternating electric field is between 1 kilohertz (KHz) and 100 KHz.

While the maximum field strength of the alternating electric field may be any field strength suitable to a particular application, in one embodiment, the maximum field strength of the alternating electric field, as measured by the peak field strength of the alternating electric field, is between about 100 V/cm and 20,000 V/cm; e.g., between 1,000 V/cm and 10,000 V/cm. Preferably, the alternating electric field is spatially non-uniform.

In an embodiment of the invention, a trapped polar analyte is released from a concentration zone, for example, by reducing the trapping strength of the alternating electric field. The trapping strength of the alternating electric field may be modulated by changing the frequency, field strength, or both. As previously indicated, another means for effecting release of an analyte involves establishment of a DC field having a polarity opposite to that of a trapped polarized analyte.

In an embodiment, subsequent to a sample or analyte concentration step according to the present invention, a further analytical step can be performed. In one embodiment, after an analyte has been concentrated in a concentration zone, the analyte is directed into an analytical separation process, for example an electrophoretic or chromatographic separation process. The concentration and localization methods of the present invention are particularly advantageous where the subsequent analytical separation process is electrophoresis because the pre-separation concentration step can provide a concentrated and narrow injection zone leading to both increased separation performance and enhanced detectability of the separated components.

In an embodiment of the present invention in which the analyte is a nucleic acid, subsequent to or during the concentration of the analyte nucleic acid in the concentration zone, the nucleic acid analyte is subjected to a nucleic acid hybridization reaction in which the concentrated nucleic acid analyte is contacted with one or more complementary nucleic acids under conditions suitable for sequence-specific hybridization. In one embodiment, the complementary nucleic acids are bound to a solid support, e.g., an array of support-bound nucleic acids including one or more potentially complementary nucleic acids. The support-bound nucleic acids may be synthetic polynucleotide probes, cDNA molecules, or any other nucleic acid or nucleic acid analog capable of sequence-specific hybridization. Exemplary arrays of support-bound nucleic acids are described elsewhere, e.g., Singh-Gasson et al., *Nature Biotechnology*, 17: 974-978 (1999); Blanchard and Friend, *Nature Biotechnology*, 17: 953 (1999); Brown et al., U.S. Pat. No. 5,807,522; each of which is incorporated herein by reference. The pre-hybridization concentration step of the present invention may result in an increased rate of hybridization, the ability to use a less concentrated sample, and/or an enhancement of the detectability of the products of the hybridization reaction. While this embodiment has been described in the context of nucleic acid hybridization, it will be apparent to one skilled in the art of biochemical instrumentation and analysis that this embodiment could be equally applied to other processes in which an analyte is contacted with a binding complement, e.g., antibody-antigen pairs, receptor-ligand pairs, biotin-avidin pairs, and the like.

Many bio-molecules in aqueous solution (e.g., suspension) are electrically charged. As is well known, force acts between two objects with charge, attractively between objects with opposite charges, repulsively between objects with similar charges. This property is exploited in certain embodiments of analyte-manipulation devices and methods of the present invention.

Under some circumstances, concentration of charged analytes on a metallic electrode may be accompanied by the generation of bubbles. In some situations, such bubbles may hinder or interfere with the desired location of the analyte proximate or on the electrode. Accordingly, some embodiments of the present invention prefer the use of electrodes with a reduced or eliminated tendency for bubble formation as compared to, say, similarly dimensioned and disposed platinum electrodes under like conditions (referred to herein, collectively, as "bubble-free" electrodes).

In an embodiment of the present invention, by establishing a DC electric current so as to establish a surface charge on the electrode that is opposite to the charge of the analyte, it is possible to attract the analyte onto and/or alongside the surface of the electrode, thereby concentrating the analyte. Or, where a gel-like electrode is employed, it is possible to attract the analyte to a region inside the electrode (e.g., via a process similar to electrokinetic injection). Upon reversing the polarity of the DC field so as to provide the electrode with a charge like that of the concentrated analyte, the concentrated analyte can be released or repelled from the electrode. One embodiment contemplates transfer of the concentrated analyte by removing a portion of the electrode upon which the analyte has become situated.

Examples of solid electrodes employable in the present invention include Pd, porous Pd, $Ni(OH)_2$, $Ni(OH)_4$, $IrO_2$. Also, ionic membranes, such as Nafion, can be used. Examples of gel-like electrode arrangements include capillary tubes or the like filed with gelatin, agarose, starch, or the like. Examples of bubble-free electrodes and electrode materials, useful in connection with the present invention, are described in co-filed patent application [Kilyk & Bowersox] and 4573/4660 [Applied Biosystems], entitled, "Bubble-Free Electrophoresis and Electroosmotic Electrodes and Devices" naming as inventors Woudenberg et al; which application is incorporated herein by reference in its entirety.

Figure 7:
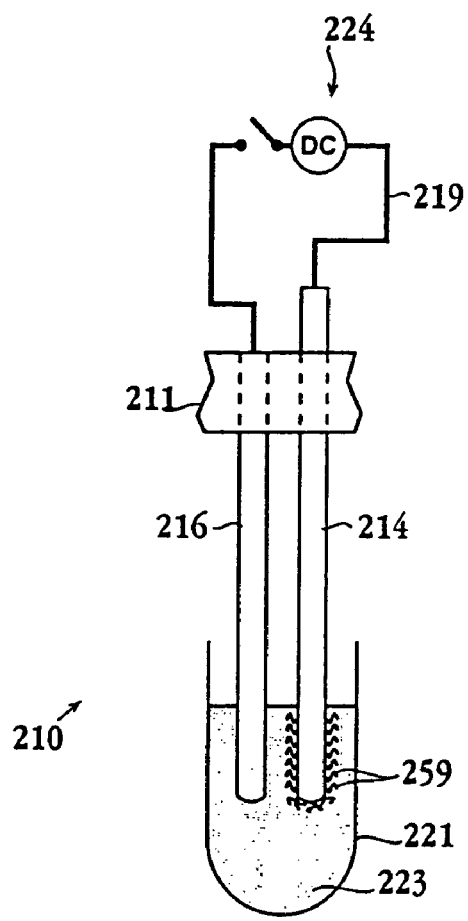
FIG. 7 is a partially schematic side view of a device for manipulating analytes, according to an embodiment of the present invention.

In an embodiment of the present invention, and with reference now to FIG. 7, an analyte-manipulation device 210 includes a first electrode 214, e.g., a bubble-free electrode as discussed above, and a second (contra) electrode 216, each connected to a DC power source 224 by way of appropriate circuitry 219. In use, electrodes 214, 216 can be placed in a solution, as shown, containing a charged analyte of interest, such as solution 223 in tube or well 221. A DC current can be established so that the charged analyte is electroplated on electrode 214, as indicated at 259.

It should be noted that the particular positioning of the contra electrode 216 is not critical. In one embodiment of the invention, the contra electrode comprises part of a vessel (e.g., a cup, well or tube) in a fashion similar to that shown in FIG. 6. It is additionally noted that it is not required that the contra electrode be bubble free (though it can be, if desired).

Figure 8:
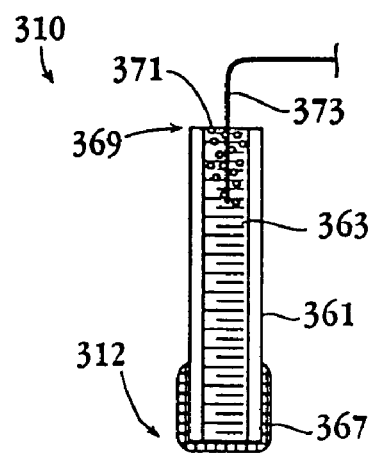
FIG. 8 is a partially schematic side view of an embodiment of a device for manipulating analytes, according to the present invention.

Referring now to FIG. 8, in an embodiment of an analyte-manipulation device according to the present invention, denoted generally by the reference numeral 310, a bubble-free electrode comprises a capillary or tube 361 (e.g., glass, fused silica, quartz) filled with an electrolyte 363. One end 312 of the capillary 361 is covered by an ionic membrane 367 (e.g., Nafion, or the like). The other end 369 is configured to receive an electrically conductive element 373 (e.g., a Pt wire) therein, in contact with the electrolyte 363. In one embodiment, upper end 369 is vented, e.g., open to the atmosphere. An advantage of such an arrangement is that bubbles that might be generated during operation of the device, as indicated at 371, can be vented to the atmosphere. Any suitable contra electrode arrangement (not shown) can be employed. In operation, device 310 can be placed in a solution containing a charged analyte of interest, and a DC current can be established so that the charged analyte is attract to and collected on the ionic membrane 367.

As an alterative to the ionic membrane, or in addition thereto, a meltable plug that selectively allows passage of small ions but not of macromolecular analytes can placed in a region of end 312. For example, a meltable plug as disclosed in U.S. Pat. No. 5,593,559 (incorporated herein by reference) can be placed at one or more regions inside the capillary.

In an embodiment of the invention, referring now to FIGS. 9A-9C, a capillary or tube 461 is provided having one end 412 defining an orifice and a second end 469 disposed for communication with a pump 474, via an interposed conduit 475. Any suitable pump can be employed, such as the illustrated piston-type pump having a piston configured for reciprocal movement in the axial direction of a cylindrical reservoir. Pump 474 is adapted for pressure-filling the conduit and capillary with a gel-like electrolyte substance, denoted as 463. The electrolyte substance 463, in turn, is disposed for communication with a current source. Such communication can be by any suitable means, and is preferably one that is not associated with any substantial amount of bubble formation. For example, a bubble-free electrode (as at 473) or a porous membrane can be employed. In an embodiment, the capillary or conduit containing the electrolyte is provided with structure permitting electrical contact through ionic movement, as described in U.S. Re 35,102, incorporated herein by reference. In one embodiment, GORE-TEX microporous PTFE tubing is utilized.

In operation, device 410 can be placed with the orifice at end 412 submerged in a solution containing a charged analyte of interest (not shown). A DC current can be established so as to attract the charged analyte for collection on the gel. The concentrated analyte can then be moved to a desired location and released by applying a reverse (repelling) voltage. The device can then be refreshed by operating the pump so as to force a portion of gel out through the open end of the capillary (see FIG. 9B), which forced-out portion can then be removed (see FIG. 9C). It should be appreciated that, in some cases, it may be desirable to dispense the analyte along with the gel. In an embodiment, the concentrated analyte is moved to a desired location and released by pumping the gel-like slug. In one such embodiment, for example, the gel-like slug is a gelatin material through which DNA does not migrate, and is melted once dispensed. Alternatively, an entangled polymer can act as a stacking media, being diluted once dispensed. Such dilution can change the permeability of the polymer, thereby permitting it to act as a stacking media.

In an embodiment, electrically-conductive members of the device of the invention (e.g., members 14, 16 of device 10 in FIG. 1; members 214, 216 of device 210 in FIG. 7) are formed or treated so as to exhibit desired wettability characteristics. For example, selected regions of members 14, 16 (FIG. 1) can be provided with a surface that is hydrophilic, i.e., wettable. For example, selected regions of the surfaces of members 14, 16 can be formed of a hydrophilic material and/or treated to exhibit hydrophilic characteristics. In one embodiment, the surfaces have native, bound or covalently attached charged groups.

Alternatively, or in addition, selected regions of members 14, 16 can be provided with exterior surface regions that are hydrophobic, i.e., one that causes aqueous medium deposited on the surface to bead. For example, selected regions of the exterior surfaces of members 14, 16 can be formed of a hydrophobic material and/or treated to exhibit hydrophobic characteristics. A variety of known hydrophobic polymers, such as polystyrene, polypropylene, and/or polyethylene, can be utilized to obtain the desired hydrophobic properties. In addition, or as an alternative, a variety of lubricants or other conventional hydrophobic films can be applied to a member's exterior surface.

In an embodiment, upper regions of the members 14, 16 are treated so as to be hydrophobic and, optionally, lower regions of the members are treated so as to be hydrophilic.

It should be appreciated that instead of, or in addition to, having the electrically-conductive members adapted for movement toward and/or away from a sample holder, such as a tube or well; the sample holder can be adapted for movement.

All publications, patents, and patent applications mentioned herein are hereby incorporated by reference to the same extent as if each individual publication, patent, or patent application was specifically and individually indicated to be incorporated by reference.

Those having ordinary skill in the art will readily understand that many modifications are possible in the disclosed embodiments without departing from the teachings thereof. All such modifications are intended to be encompassed within the scope of the following claims.

The invention claimed is:

1. A method comprising:
    generating an alternating electric field, between two co-extensive, elongated, electrically-conductive members;
    capturing polarizable cells in a sample, in the alternating electric field, between the two co-extensive, elongated, electrically-conductive members, and
    removing the two co-extensive, elongated, electrically-conductive members with the polarizable cells captured therebetween, from the sample, while maintaining the alternating electric field.

2. The method of claim 1, wherein the sample comprises a complex mixture.

3. The method of claim 1, wherein the alternating electric field has a time-averaged, integrated field strength that is zero when taken over one complete cycle.

4. The method of claim 1, further comprising, contacting the sample with a binding component before removing the two co-extensive, elongated, electrically-conductive members.

5. The method of claim 1, further comprising:
    applying a first direct current electric field to the co-extensive, elongated, electrically-conductive members prior to generating the alternating current electric field.

6. The method of claim 5 further comprising applying a second direct current electric field, oppositely charged relative to the first direct current electric field, to the co-extensive, elongated, electrically-conductive members after removing the co-extensive, elongated, electrically-conductive members.

7. The method of claim 1, wherein the polarizable cells are captured in a tip region of the two co-extensive, elongated, electrically-conductive members.

8. The method of claim 1, wherein the polarizable cells are present in a buffered electrolyte solution.

9. The method of claim 1, wherein the removing comprises holding the device in an operator's hand.

10. The method of claim 1, wherein the method further comprises, moving at least one of the co-extensive, elongated, electrically-conductive members between a cell pick-up position and a cell deposition position.

11. The method of claim 1, wherein the capturing comprises concentrating a plurality of cells between the co-extensive, elongated, electrically-conductive members.

12. The method of claim 1, wherein the capturing comprises capturing a plurality of cells between a plurality of pairs of co-extensive, elongated, electrically-conductive members.

13. The method of claim 1, wherein the two co-extensive, elongated, electrically-conductive members are separated from one another by a distance of between about 20 micrometers and 2 millimeters.

14. The method of claim 1, wherein the two co-extensive, elongated, electrically-conductive members are separated from one another by a distance of from 20 micrometers to 1.50 millimeters.

15. The method of claim 1, wherein the two co-extensive, elongated, electrically-conductive members are separated from one another by a distance of between 100 micrometers and 0.75 millimeter.

16. The method of claim 1, wherein the two co-extensive, elongated, electrically-conductive members are separated from one another by a distance of between about 0.75 millimeter and 1.0 millimeter.

* * * * *